United States Patent
Cutler

[11] Patent Number: 5,095,849
[45] Date of Patent: Mar. 17, 1992

[54] GLOVE MAKING APPARATUS

[76] Inventor: Sam Cutler, 405 N. Ocean Blvd., Apt. 904, Pompano Beach, Fla. 33062

[21] Appl. No.: 540,478

[22] Filed: Jun. 19, 1990

[51] Int. Cl.$^5$ .......................... A61K 7/40; B05B 1/14
[52] U.S. Cl. .................... 118/326; 264/222; 264/301
[58] Field of Search ................. 264/222, 301; 118/326

[56] References Cited

U.S. PATENT DOCUMENTS

| | | | |
|---|---|---|---|
| 2,508,156 | 5/1950 | Gilman | 264/222 |
| 2,789,933 | 4/1957 | Bargmeyer | 264/301 |
| 3,100,724 | 8/1963 | Rocheville | 118/326 |
| 4,913,897 | 4/1990 | Chvapil et al. | 264/222 |

*Primary Examiner*—Willard Hoag
*Attorney, Agent, or Firm*—Kirschstein, Ottinger, Israel & Schiffmiller

[57] ABSTRACT

Gloves are made in situ on human hands by applying a glove-making fluid composition completely about the entire expanse of the hands within a chamber of an enclosure. The fluid composition solidifies to form glove-like coatings upon exposure to air.

10 Claims, 2 Drawing Sheets

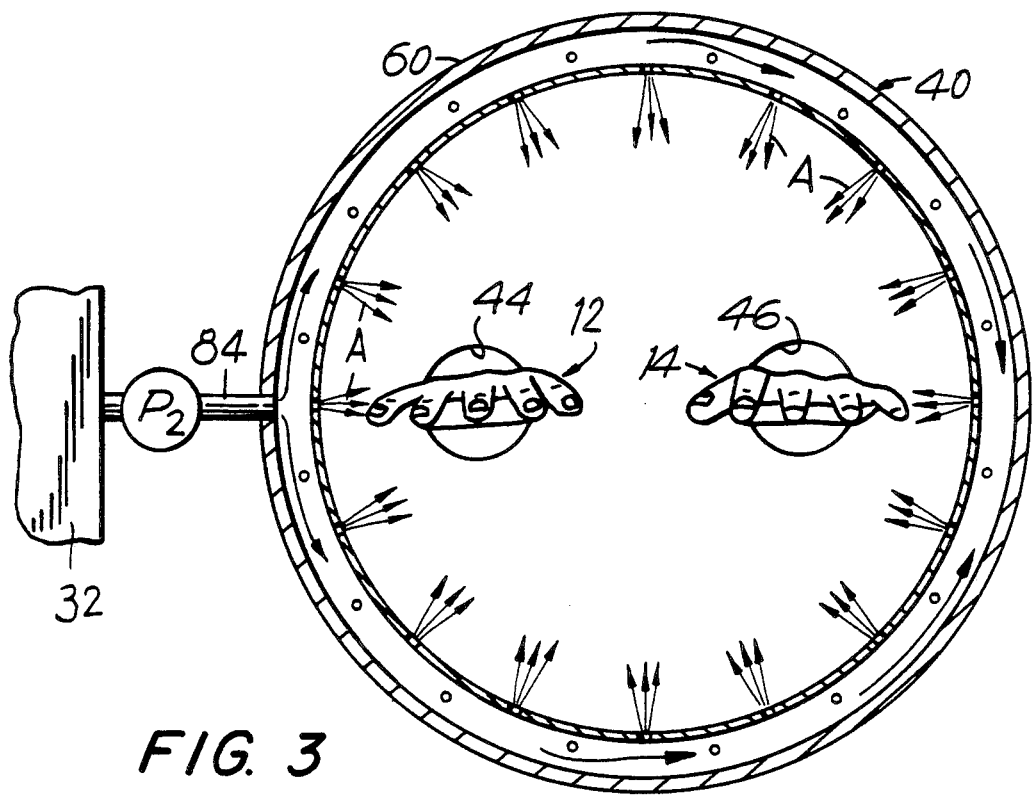
FIG. 3
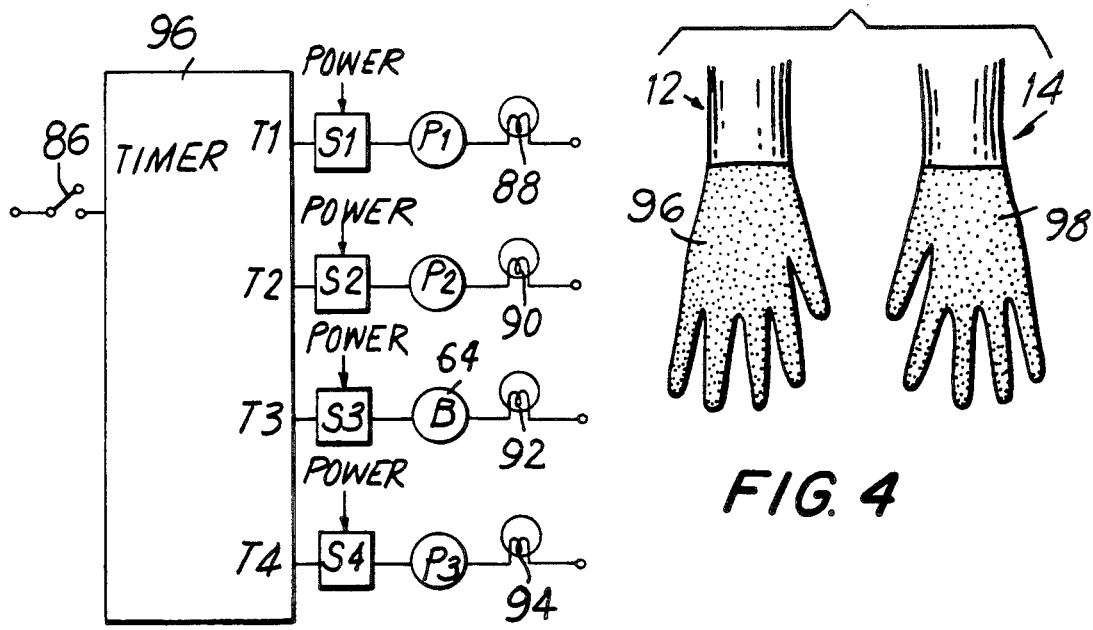
FIG. 4
FIG. 5

GLOVE MAKING APPARATUS

BACKGROUND OF THE INVENTION

1. Field of the Invention

This invention generally relates to an apparatus for, and a method of, making a glove in situ on a human hand.

2. Description of Related Art

There are many applications where a hand-forming elastic glove is desirable. For example, surgeons and medical attendants require such gloves to freely move their fingers when wearing the gloves while retaining tactile sensation through the gloves. The elasticity of the gloves enables better fit, and the flexibility provides a better feel and secure gripping of tools, workpieces and the like.

Gloves are typically woven, knit, molded or otherwise made at a manufacturer's facility, and then packed and shipped to a user who dons the gloves prior to using them for their intended purpose. This is not altogether satisfactory, since different users have differently sized hands. Gloves would have to be made in a correspondingly large number of sizes to properly fit the hands of all intended users. As a practical matter, gloves are not made, ordered or stocked in multiple sizes and, even if they were, there is such a wide variety in the lengths, sizes and spacings of the individual fingers for different users that, at best, the fit for a particular user represents a compromise. To a certain extent, the fit problem is alleviated by using elastic or rubber gloves which stretch to conform to the dimensions of a particular person's hand. However, even so, the elastic material stretches to a different extent at different portions of the gloves and weakens the gloves at those stretched portions.

It is known from U.S. Pat. No. 3,577,516 to form a strong, tough, adherent bandage in situ on a wound by separately or simultaneously spraying a water-insoluble polymer and a plasticizer or solvent therefor over the wound. When the spray-on mixture sets, a 10-mil bandage is formed over the wound.

It is known from U.S. Pat. No. 2,313,807 to form finger coatings by immersing one's fingertips in a colloidal solution of latex, and then by withdrawing one's fingers from the solution and allowing the solution to solidify.

It is also known from U.S. Pat. No. 2,810,161 to produce seamless cosmetic gloves employed as coverings for prosthetic hands or as coverings for hand injuries which have resulted in disfigurement of a natural hand.

It is also known from U.S. Pat. No. 3,048,169 to form a cast in situ on a living body from a sheet of polymerized foam plastic.

It is further known from U.S. Pat. No. 3,563,228 to form adherent films, such as collagen, on animal tissue.

SUMMARY OF THE INVENTION

1. Objects of the Invention

It is a general object of this invention to make a glove in situ on a human hand.

It is another object of this invention to make a glove which exactly conforms to the size and shape of an intended wearer's hand.

Another object of this invention is to provide a hand-conforming glove with better tactile feel and more secure gripping of tools, workpieces and the like.

A further object of this invention is to provide a novel apparatus for, and a method of, making a glove.

2. Features of the Invention

In keeping with these objects, and others which will become apparent hereinafter, one feature of this invention resides, briefly stated, in an apparatus for, and a method of, making a glove in situ on a human hand. The invention includes an enclosure having walls bounding a chamber, as well as an access opening extending through one of the walls. The access opening permits insertion of the hand into the chamber. The invention further comprises means for applying a glove-making fluid composition completely about the entire expanse of the hand within the chamber. The fluid composition is a film-forming liquid such as latex or other synthetic material. For example, natural latex, such as Lotol 1185 can be used. Latexes of other elastomeric material such as polyacrylates, e.g. polyethyl acrylate, polybutadiene, styrene-butadiene copolymer, acrylonitrile-butadiene rubber, and neoprene (polychloroprene) can be employed for this purpose. Preferably, the fluid composition is a colloidal solution of rubber or latex in a volatile solvent containing sufficient ammonia to prevent coagulation of the latex when not directly exposed to the air, but insufficient to prevent coagulation when a thin film of the solution is exposed to the air.

Consequently, the fluid composition quickly solidifies to form a glove-like coating in situ on the hand within the chamber. The coating is sufficiently flexible and resilient, and thin, e.g. on the order of 10 mils, so as to retain tactile sensation through the glove-like coating.

In the preferred embodiment, the fluid composition is sprayed under pressure onto the hand within the chamber. A plurality of nozzles are arranged in an annulus around the hand within the chamber. A pump conveys the fluid composition under pressure from a reservoir through the nozzles from which the fluid composition emerges as a fine mist or cloud which completely envelopes the hand within the chamber. Excess fluid composition that falls from the hand is collected and drained from the chamber.

Another feature of this invention resides in expediting the solidification of the fluid composition by providing means for drying the fluid composition. A hot-air blower is operative for conveying and directing heated air onto the hand.

Still another feature of this invention resides in rinsing the hand within the chamber with a rinse fluid prior to applying the fluid composition thereon. The rinse fluid is essentially a cleaning or sterilizing fluid, and may also be a solvent in order to facilitate removal of the glove-like coating from the hand after its intended use has been finished.

In order to confine the mist or cloud to the enclosure, means are provided at the access opening for sealingly engaging the wrist of the hand. A resilient cuff closely engages the wrist of the inserted hand and rises above the one wall that contains the access opening.

The rinsing, applying and drying procedures are separately performed successively in separate operational modes. Indicators, such as lamps, are provided for visually indicating which operational mode is currently in progress. In the preferred embodiment, two access openings are provided in the enclosure, one for each hand, and the fluid composition is simultaneously applied completely about both hands within the chamber so that a pair of gloves are formed.

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 3 is an enlarged, part sectional view taken on line 3—3 of FIG. 2;

FIG. 4 is a view of a pair of outstretched hands provided with gloves according to this invention; and FIG. 5 is an electrical schematic of a control circuit for controlling the different operational modes of making a glove in accordance with this invention.

DETAILED DESCRIPTION OF THE PREFERRED EMBODIMENTS

Figure 1:
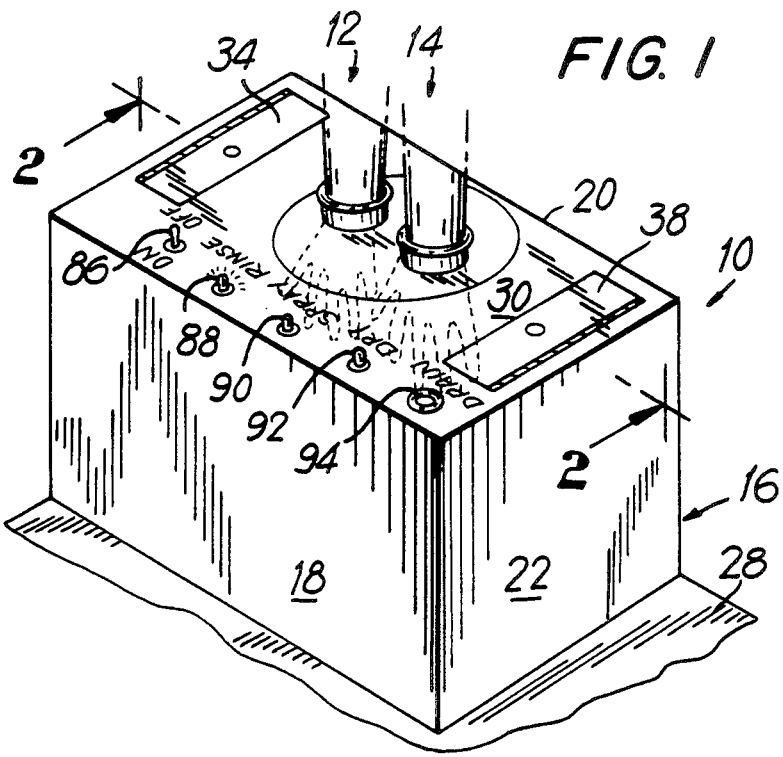
FIG. 1 is a front, side and top perspective view of an apparatus for making a glove in situ on a human hand in accordance with this invention.

Turning now to the drawings, reference numeral 10 generally identifies an apparatus for making a glove in situ on a human hand, and preferably on two hands 12, 14 simultaneously. Apparatus 10 includes a housing 16 of generally parallelepiped shape having a front wall 18, a rear wall 20, a pair of opposite side walls 22, 24, a bottom wall 26 resting on a support surface 28, and a top wall 30.

Figure 2:
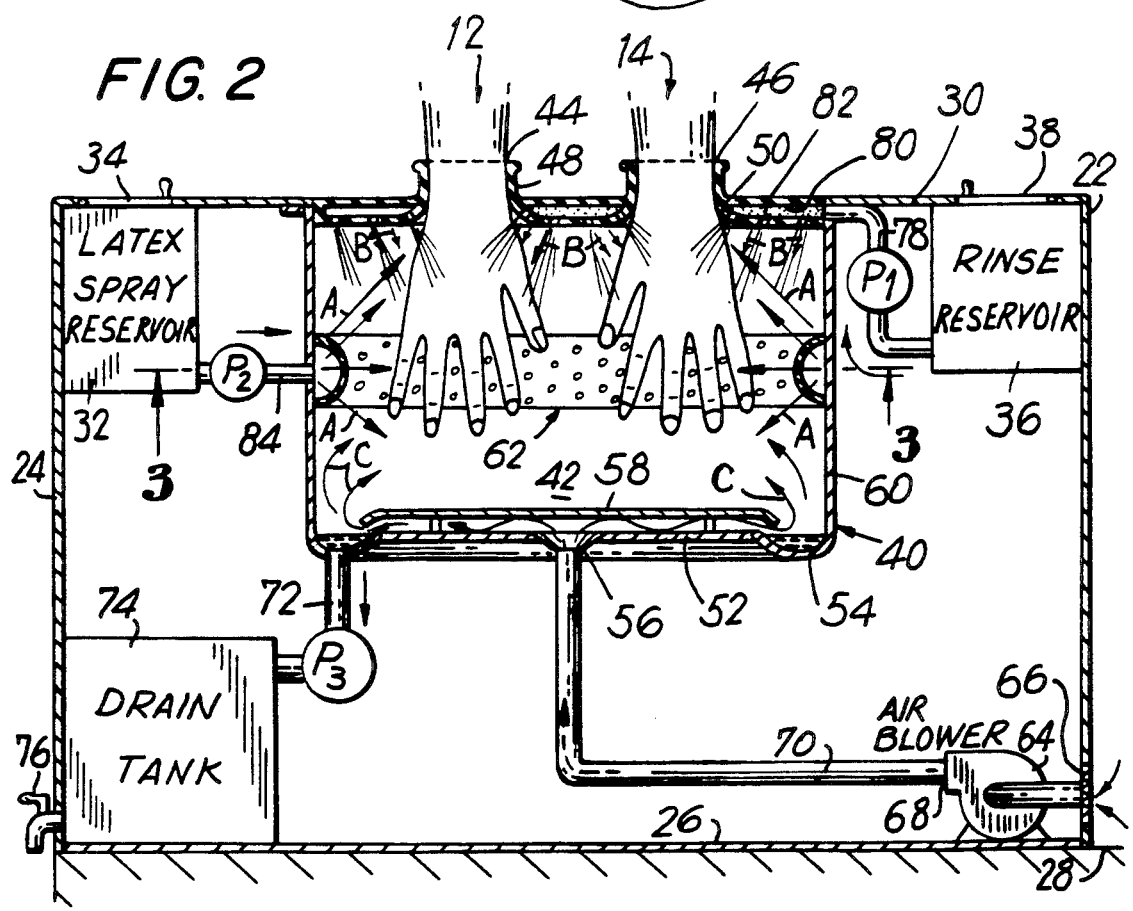
FIG. 2 is an enlarged, part sectional view taken on line 2—2 of FIG. 1.

As best shown in FIG. 2, a reservoir 32 is located within the housing 16. Access to the reservoir 32 is obtained by opening a door 34 which is pivotably mounted on the top wall 30 for movement between open and closed positions. In the closed position, door 34 is flush with the top wall 30.

Reservoir 32 is filled with a glove-making fluid composition. The fluid composition is a film-forming liquid such as latex or other synthetic material. For example, natural latex, such as Lotol 1185 can be used. Latexes of other elastomeric material such as polyacrylates, e.g. polyethyl acrylate, polybutadiene, styrene-butadiene copolymer, acrylonitrileburadiene rubber, and neoprene (polychloroprene) can be employed for this purpose. Preferably, the fluid composition is a colloidal solution of rubber or latex in a volatile solvent containing sufficient ammonia to prefent coagulation of the latex when not directly exposed to the air, but insufficient to prevent coagulation when a thin film of the solution is exposed to the air.

Another reservoir 36 is also mounted within the housing 16, and is filled with a rinse fluid. Access to the reservoir 36 is obtained by opening a door 38 which is pivotably mounted on the top wall 30 for movement between open and closed positions. In the closed position, door 38 is flush with the top wall 30. The rinse fluid is a cleaning or sterilizing fluid, and may advantageously be water or a solvent in order to facilitate removal of the gloves after their intended use.

The housing 16 also supports an enclosure 40 having walls bounding a chamber 42. Access openings 44, 46 extend through the top wall 30, and permit insertion of the individual hands 12, 14 into the chamber 42. Resilient cuffs 48, 50 extend through the access openings 44, 46 for a predetermined distance above the top wall 30. The cuffs sealingly engage the wrists of the hands within the chamber.

The enclosure 40 has a base wall 52 which is formed with an annular trough 54 for collecting excess fluid composition, as explained below. The base wall 52 also is formed with an air inlet 56, which is overlain by an air baffle 58 whose operation is described below.

Enclosure 40 also has an annular side wall 60 on which an annular manifold 62 is mounted. Manifold 62 includes a plurality of nozzles uniformly distributed around the inserted hands. The manifold 62 has a semicircular cross-section with the nozzles distributed on upper, middle and lower portions thereof. The nozzles direct the fluid composition therefrom in the direction illustrated by the arrows A as a mist or cloud which completely envelopes the inserted hands.

The housing 16 also contains an air blower 64 having a blower inlet 66 in communication with the ambient environment, and a blower outlet 68 connected by a conduit 70 to the air inlet 56. Another conduit 72 connects the trough 54 to a drain tank 74 also mounted within the housing 16. A drain cock 76 permits draining of the tan 74 to the exterior environment.

The rinse reservoir 36 is connected by a conduit 78 to an upper compartment 80 of the enclosure 40. The compartment 80 is bounded at one side by the top wall 30, and on its opposite side by the cuffs 48, 50. The cuffs are formed with a plurality of apertures 82 operative for emitting the rinse fluid toward the hands inserted within the chamber 42 in the direction of the arrows B. A pump P1 conveys the rinse fluid from the reservoir 36 under pressure along the conduit 78.

The fluid composition reservoir 32 is connected by a conduit 84 to the nozzle manifold 62. A pump P2 in the conduit 84 conveys the fluid composition under pressure to the manifold 62.

Another pump P3 is provided in the conduit 72 for conveying excess fluid composition collected in the trough 54 for delivery to the drain tank 74 for eventual disposal.

As further shown in FIG. 1, an on/off control switch 86 is mounted on the top wall together with a row of indicator lamps including rinse lamp 88, spray lamp 90, dry lamp 92 and draim lamp 94, all being successively and separately lit to indicate which operational mode is currently in progress in the formation of the pair of gloves.

The operation of the apparatus according to this invention will be described with the aid of the electrical schematic depicted in FIG. 5. Initially, the on/off control switch 86 is actuated from the off to the on position, thereby energizing a timer 96. The timer 96 is operative for generating output signals during four different time intervals T1, T2, T3, T4. The output signals T1, T2, T3, T4 are connected to four separate switches S1, S2, S3, S4 which, in turn, are respectively connected to pump P1, pump P2, the air blower 64, and the pump P3 and, in turn, are respectively connected to indicator lamps 88, 90, 92, 94.

The timer output signal T1 closes the normally open switch S1 and permits electrical power to be conducted to the pump P1. Pump P1 conducts the rinse fluid from the reservoir 36 along the conduit 78 under pressure to the chamber 80, whereupon the rinse fluid is ejected under pressure in the direction of the arrows B toward the hands 12, 14 inserted within the chamber 42 through the apertures 82. The output signal T1 lasts for a predetermined time, for example, 10 seconds. The rinse lamp 88 is illuminated during this time period, thereby alerting the user that the rinse mode is in progress.

The timer output signal T2 thereupon closes the normally open switch S2 and permits electrical power to be conducted to the pump P2. Pump P2 conducts the fluid composition from the reservoir 32 along the conduit 84 under pressure to the manifold 62, whereupon the fluid composition is ejected under pressure in the direction of the arrows A toward the hands 12, 14 inserted within the chamber 42 through the nozzles as a fine enveloping mist or cloud. The output signal T2 lasts for a predetermined time, for example, 15 seconds. The spray lamp 90 is illuminated during this time period, thereby alerting the user that the spray mode is in progress. The resilient cuffs 48, 50 effectively seal the interior of the enclosure 40 due to their sealing engagement with the wrists of the hands 12, 14 during the spray mode. Fluid composition that falls from the hands, i.e. so-called waste or excess fluid, is collected in the annular trough 54. The baffle 58 prevents such waste fluid from entering the air inlet 56.

The timer output signal T3 thereupon closes the normally open switch S3 and permits electrical power to be conducted to the blower 64. The blower 64 sucks air through blower inlet 66 and heats the air prior to delivering the heated air under pressure along conduit 70 to air inlet 56 where the heated air is directed by the baffle 58 in the direction of the arrows C toward the hands 12, 14 inserted within the chamber in order to expedite the solidification of the fluid composition on the hands due to exposure with the heated flowing air. The timer output signal T3 lasts for a predetermined time period, for example, 60 seconds. The dry lamp 92 is illuminated during this time to indicate to the user that the drying mode is in progress.

The timer output signal T4 thereupon closes the normally open switch S4 and permits electrical power to be conducted to the pump P3. The pump P3 conducts the excess fluid composition from the trough 54 along the conduit 72 under pressure to the drain tank 74, whereupon opening of the cock 76 permits evacuation of the tank 74. The output signal T4 lasts for a predetermined time, for example, 10 seconds. The drain lamp 94 is illuminated during this time period, thereby alerting the user that the drain mode is in progress.

The user may now remove his hands from the chamber 42. As best shown in FIG. 4, the solidified fluid composition forms glove-like coatings 96, 98 in situ on both hands.

In another embodiment, rather than spraying the fluid composition onto the hands, the hands can be immersed in a bath of the fluid composition.

The gloves need not stop at the wrists, but can extend up the arms to the elbows.

Rather than inserting both hands into a single chamber, a partition wall may be provided for subdividing the chamber into two separate sub-chambers, one for each hand.

It will be understood that each of the elements described above, or two or more together, also may find a useful application in other types of constructions differing from the types described above.

While the invention has been illustrated and described as embodied in a glove making apparatus and method, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims:

1. An apparatus for making a glove in situ on a human hand, comprising:
   (a) an enclosure having walls bounding a chamber, and an access opening extending through one of the walls and permitting insertion of the hand into the chamber;
   (b) means for applying a glove-making fluid composition completely about the entire expanse of the hand within the chamber, said fluid composition solidifying to form a glove-like coating in situ on the hand within the chamber; and
   (c) means for rinsing the hand within the chamber with a rinse fluid prior to operation of the applying means.

2. The apparatus according to claim 1, wherein the applying means includes a reservoir for the glove-making fluid composition, and means for spraying the fluid composition under pressure onto the hand within the chamber.

3. The apparatus according to claim 2, wherein the spraying means includes a pump and a plurality of nozzles arranged in an annulus within the chamber.

4. The apparatus according to claim 1; and further comprising means for collecting excess fluid composition that falls from the hand within the chamber, and for conveying the excess fluid composition from the chamber.

5. The apparatus according to claim 1; and further comprising means for drying the fluid composition applied to the hand within the chamber.

6. The apparatus according to claim 5, wherein the drying means includes a hot air blower operative for conveying heated air to the chamber, and means for directing the heated air onto the hand within the chamber to expedite the solidification of the fluid composition on the hand due to exposure to the heated air.

7. The apparatus according to claim 1; and further comprising means at the access opening for sealingly engaging the wrist of the hand within the chamber.

8. The apparatus according to claim 1, wherein the enclosure has two access openings, one for each hand, and wherein the applying means simultaneously applies the fluid composition completely about both hands within the chamber.

9. The apparatus according to claim 1; and further comprising means for drying the fluid composition applied to the hand within the chamber; and wherein the rinsing means, applying means and drying means are respectively and separately operable in rinse, apply and dry modes of operation.

10. The apparatus according to claim 9; and further comprising mean for indicating which mode of operation is in progress.

* * * * *